US00PP11107P

United States Patent [19]

Andersen et al.

[11] Patent Number: Plant 11,107

[45] Date of Patent: Oct. 19, 1999

[54] SWEET CHERRY CULTIVAR NAMED 'ROYALTON'

[75] Inventors: Robert L. Andersen; Susan K. Brown, both of Geneva; Roger D. Way, Stanley; Kenneth G. Livermore, Geneva; David E. Terry, Ovid, all of N.Y.

[73] Assignee: Cornell Research Foundation, Inc., Ithaca, N.Y.

[21] Appl. No.: 08/831,762

[22] Filed: Apr. 1, 1997

Related U.S. Application Data

[63] Continuation of application No. 08/688,776, Jul. 31, 1996, abandoned, which is a continuation of application No. 08/537,148, Aug. 21, 1995, abandoned, which is a continuation of application No. 08/240,501, May 10, 1994, abandoned, which is a continuation of application No. 08/022,881, Feb. 12, 1993, abandoned, which is a continuation of application No. 07/764,573, Sep. 18, 1991, abandoned.

[51] Int. Cl.[6] ..... A01H 5/00

[52] U.S. Cl. ..... Plt./181

[58] Field of Search ..... Plt./181

[56] References Cited

U.S. PATENT DOCUMENTS

P.P. 7,502 4/1991 Bradford et al. ..... Plt./37

OTHER PUBLICATIONS

"1982–1982 Catalog of New and Noteworthy Fruits" New York State Fruit Testing Cooperative Association, Inc.

Brown et al. "HortScience 23": 902–904 (1988) measures fruit firmness of various varieties including NY 11390.

Andersen, "Proceedings of the 136th Annual Meeting", The New York State Horticultural Society, 136: 164–166 (1991).

Andersen, Manuscript of a paper given Feb. 6, 1991 at the Orchard Show and Cherry Conference, Acme Michigan indicates NY 11390.

Program of the 73rd Annual Meeting New York State Fruit Testing Cooperative Association, Inc., Sep. 19, 1991.

*Primary Examiner*—Howard J. Locker

[57] ABSTRACT

A new and distinct variety of sweet cherry tree which produces large and firm fruit having rich, strong cherry flavor, crisp flesh and which contain large stones of round to round-conic shape. The fruit has exceptionally high levels of soluble solids at ripeness. A seeding of 'NY1725', the tree is particularly characterized as being self-unfertile, late coming into production, but which bears dark, sweet fruit that is resistant to water stress induced cracking. This vigorous tree is of upright branching habit, forms a tall pyramidal figure, and shows resistance to bacterial canker.

4 Drawing Sheets

This application is a continuation, of application Ser. No. 08/688,776, filed Jul. 31, 1996, now abandoned which is a continuation of application Ser. No. 08/537,148, filed Aug. 21, 1995, which is now abandoned, which is a continuation of application Ser. No. 08/240,501, filed May 10, 1994, now abandoned, which is a continuation of application Ser. No. 08/022,881, filed Feb. 12, 1993, now abandoned, which is a continuation of application Ser. No. 07/764,573, filed Sep. 18, 1991, now abandoned.

BACKGROUND OF THE INVENTION

This invention is a new and distinct cultivar of sweet cherry 'Royalton', which we discovered in a test planting belonging to the New York State Agricultural Experiment Station, Cornell University, Geneva, Ontario County, N.Y. This discovery is a product of a cherry breeding research program of the New York State Agricultural Experiment Station ("Station").

In 1968 open-pollinated seed from unknown male parent source was gathered from a NY1725 cherry tree growing on 'Station' property. This seed was given cold treatment to satisfy its stratification requirement along with other seeds derived from our research. It was planted in Research Field Number D-1 Row-19, Tree-161 on Station grounds. When the tree resulting from this seed bore fruit in 1975 we selected it because it had unique fruit. It was designated NY11390 and grafted in 1976 utilizing two different grafting techniques, topworking and nursery T-budding. One top-worked, grafted tree was constructed by grafting onto NY5389 which become the interstem. This tree was located in the Station research field designated as Lucey in Row 6, Tree 16 (abbreviated as LR6T16). Three grafted trees resulted from "T" budding onto "Mahaleb" rootstocks in the nursery. These were harvested in 1980 and stored in Station tree storage facilities until the spring of 1981 when they were planted in a Station research location designated as Crittenden Number 30, Row 7, Trees 25, 26, and 27 (abbreviated as C30R7T25, T26 and T27). The trees located at LR6T16 and C30R7T25 and T26 subsequently fruited and had research observations taken about their performance on a regular, annual basis, and were identical to one another in all horticultural respects that were noted by the various technicians and faculty scientists who took observations on them. The tree located at C30R7T27 died without providing any important evaluation records. C30R7T25 is still alive and in a sufficiently good state of health to afford useful performance evaluation records. Further trees were propagated by Station technicians in 1984 using plant parts taken from the NY 11390 trees located in LR6T16. These trees were planted in the spring of 1986 in a Station research field designated Lucey Number 50, Row 4, Trees 1 through 7. Other 'Royalton' trees from our nursery propagation were distributed during the 1980s to private orchardist-cooperators for the purpose of testing using a restricted distribution test agreement. Trees of NY11390, including a few hundred trees asexually propagated by grafting, in evaluations prior to filing of the patent application herein were consistantly found to be true-to-type and stable in their horticultural traits. Since the patent application was submitted in 1991, vegetative buds of 'Royalton' have been provided to commercial fruit tree nurseries, and a breeder-inventor herein has seen commercial orchards of 'Royalton' and has seen no change in traits from those that were noted in evaluations prior to the patent application being submitted.

COMPARISON OF RELATED ART

In all of the test plantings, trees of 'Royalton' bore unusually large fruit with excellent fruit quality as judged by experienced researchers and cherry orchardists. These trees were more resistant to water stress induced fruit cracking and bacterial canker than most other selections and cultivars which we tested. Trees of 'Royalton' have been slower to start setting a fruit crop than were many other sorts we had under test. While of questionable value to orchardists, this lack of precocity is a distinguishing feature of 'Royalton'. Trees of 'Royalton' are more vigorous than most other sorts of cherries that we have had under test. 'Royalton' produces a characteristic type of tree habit that we describe generally as upright and slightly barren of fruiting spurs on wood three years old and older. To our knowledge there is no other cultivar which has the same combination of tree growth habit and fruit and fruiting characteristics as this invention. The reduction in spur numbers reduces total fruit yield and increases the fruit size, but since cherries are not thinned by hand or with plant growth regulators, thinning requirements are not affected. Table 1 shows a comparison of four fruit traits of 29 sweet cherry cultivars and selections including 'Royalton' (NY 11390). It is cited from S. K. Brown and M. C. Bourne, 1988. Assessment of components of fruit firmness in selected sweet cherry genotypes. HortScience 23(5) :902–904.

| Cultivar or Selection | Flesh (N) | Total (N) | SSC (% Brix) | FRF (g) |
|---|---|---|---|---|
| Moreau | 1.28 a | 3.73 ef | 14.2 mn | 609 bc |
| NY 6476 | 1.21 ab | 4.17 bcd | 16.5 fgh | 422 f–j |
| Emperor Francis | 1.13 b | 4.44 ab | 17.4 cde | 550 d |
| Ulster | 0.97 c | 4.22 bc | 19.1 ab | 466 ef |
| NY 3801 | 0.97 c | 3.20 ijk | 13.7 n | 632 ab |
| Rainier | 0.95 c | 3.91 de | 17.0 d–g | 435 f–i |
| NY 9801 | 0.80 d | 3.77 ef | 18.9 ab | 419 g–k |
| NY 1507 | 0.79 d | 4.66 a | 19.4 a | 391 ijk |
| NY 5929 | 0.78 d | 3.18 ijk | 19.4 a | 342 lm |
| NY 3308 | 0.78 d | 3.21 ij | 15.9 hij | 489 c |
| Hudson | 0.77 de | 3.90 de | 17.7 cd | 569 cd |
| Bing | 0.76 de | 3.38 ghi | 19.1 ab | 326 m |
| Schmidt | 0.76 de | 3.42 ghi | 18.6 b | 397 h–k |
| Cavalier | 0.74 def | 3.93 cde | 15.5 jk | 465 ef |
| Van | 0.73 def | 2.78 mn | 18.9 ab | 436 fgh |
| Starkrimson | 0.72 d–g | 3.41 ghi | 14.0 n | 611 bc |
| Royalton | 0.69 c–h | 3.05 j–m | 19.4 a | 554 d |
| Sam | 0.66 f–j | 3.35 hi | 14.9 klm | 658 a |
| Bada | 0.63 g–j | 3.56 fgh | 17.3 cde | 430 f–j |
| NY 7679 | 0.62 hij | 3.20 ijk | 17.1 def | 270 n |
| Windsor | 0.58 ijk | 2.92 k–n | 15.8 ij | 419 g–k |
| Stella | 0.55 jkl | 3.21 lj | 16.0 hij | 573 cd |
| Victor | 0.54 jkl | 3.67 efg | 15.0 kl | 498 e |
| Viva | 0.51 klm | 3.13 i–l | 16.9 efg | 386 jkl |
| Hedelfingen | 0.49 klm | 2.88 lmn | 14.8 lm | 412 h–k |
| Merton Reward | 0.48 lm | 3.03 j–m | 16.4 ghi | 380 kl |
| May Duke | 0.43 mn | 2.67 no | 17.9 c | 501 c |
| Early Rivers | 0.42 nm | 2.34 p | 13.9 n | 460 efg |
| Merton Bounty | 0.39 n | 2.39 op | 17.0 d–g | 426 f–j |

NY3308 referred to in Table 1 has been named 'Hartland' and is the subject of plant patent application Ser. No. 08/835,640, and NY 6476 referred to in Table 1 has been named 'Somerset' and is the subject of plant patent application Ser. No. 08/876,370.

DESCRIPTION OF THE INVENTION

Pollination

We have conducted experiments to determine the pollination biology specifics about 'Royalton'. Our experiments took the form of field tests to cover the opening flowers with paper bags and thereby isolate flowers of 'Royalton' from bee visitation. Such bagging allowed us to subsequently apply pollen derived from known sources to the flower stigmas to determine the specific pollination compatibility group to which 'Royalton' belongs. It is self unfruitful and belongs to Group II as described by Crane and Brown, 1955 [*Sci. Hort.* 11:53–5]. Suitable known pollinator varieties with bloom dates that overlap those of the instant tree are 'Stella', 'Somerset', 'Hartland', 'Bing' and 'Napoleon' (synonym is 'Royal Ann'). The only known ineffective pollinator with overlapping bloom date is 'Schmidt' which causes 'Royalton' to set very poor crops. The pollinators have to be planted in close enough proximity to work effectively. Most pomologists agree that the distance between pollinator and pollinatee should not be more than two or three trees.

Electrophoretic Enzyme Tests

We conducted electrophoretic enzyme tests to determine the presence or absence of certain specific enzymes. It is positive for Diaphorase (heterozygous), Glucose Phosphate Isomerase (homozygous), Aconitase (heterozygous) and 6 - Glucose Phosphogluconate Dehydrogenase (heterozygous). While other cherry cultivars or genotypes may have these same enzyme characteristics we are unaware of any reports of cultivars which are the same as 'Royalton' in this regard.

Detailed Plant Description

Accompanying figures depict leaves, flowers, fruits and a pit. The numeral color specifications employed are those of The Royal Horticultural Society Colour Chart (1976).

Flowers and Flowering

Flowers (FIG. 1) are born on terminals of spurs on branches which are two years old or older but many fewer fruiting spurs exist on three year old wood than on most other cultivars which we have tested. They are also born from axillary buds of long shoots laid down the previous growing season. Typically, 3 to 5 flowers are produced from terminal spur buds and 3 to 5 flowers are also borne on axillary buds.

Figure 1:
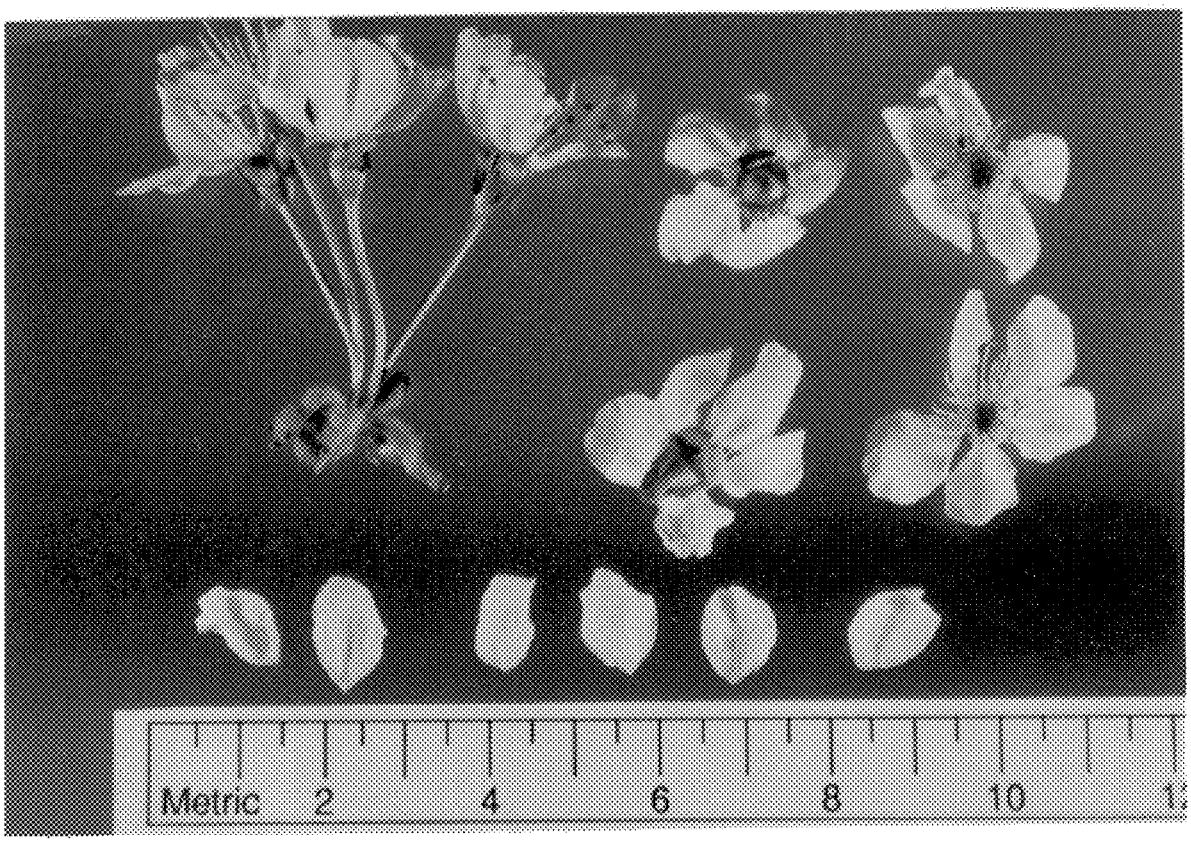
FIG. 1 shows typical flowers of 'Royalton'.

Flowers are white, single and have no unusual features that distinguish them from those of other sweet cherry cultivars. They are structurally typical of *Prunus avium,* with a base number of 5 petals and about 25 stamens. As indicated in FIG. 1, the diameter of the flowers is about 2.5 cm to 3.0 cm when fully expanded. Pedicels are about 2 cm long and of intermediate thickness, about 10 mm. Anthers are yellow 11B and pollen is yellow-orange 15 A. Self pollinations of 'Royalton' are unfruitful.

Full bloom dates at Geneva, N.Y. for 'Royalton' in 1996, 1997 and 1998 averaged about April 29 whereas full bloom dates for 'Somerset' for the same period in Geneva, N.Y. averaged about April 27 while full bloom dates for 'Hartland' for the same period in Geneva, N.Y. averaged about May 1. The bloom dates of 'Royalton' overlap sufficiently with those of 'Somerset' and 'Hartland' for effective pollination. The bloom period varies greatly by season. In two, unusually hot spring seasons during the 1990s, time between 10% bloom and 100% bloom was one day. In cool seasons, the time is four to five days. First bloom on 'Royalton' trees with Mazzard rootstocks is usually in year seven in the orchard after graft placement in the nursery when the nursery is located in a climate such as that in Geneva, N.Y. where two-year grow-out of nursery trees is necessary. If the nursery trees are grown in California or other climates where one-year grow-out is possible subsequent to dormant season bench-grafting or spring grafting, one year is subtracted from the length of time from graft placement compared to the two-year grow-out cases on either Mazzard or more precocious rootstock cultivars such as 'Gisela 5'.

Fruiting Habit and Fruit

'Royalton' trees which are grafted to the common cherry rootstock, 'Mazzard Seedling' (Mazzard), typically do not produce flowers for at least two growing seasons after orchard planting. Fruit is seldom set on trees which flower for their first time. It is common for fruit set to be delayed on 'Royalton'/Mazzard trees until the sixth season. This slowness to bear flowers and set fruit, termed "lack of precociousness," is a unique feature of 'Royalton' when it is grafted to Mazzard.

Figure 2:
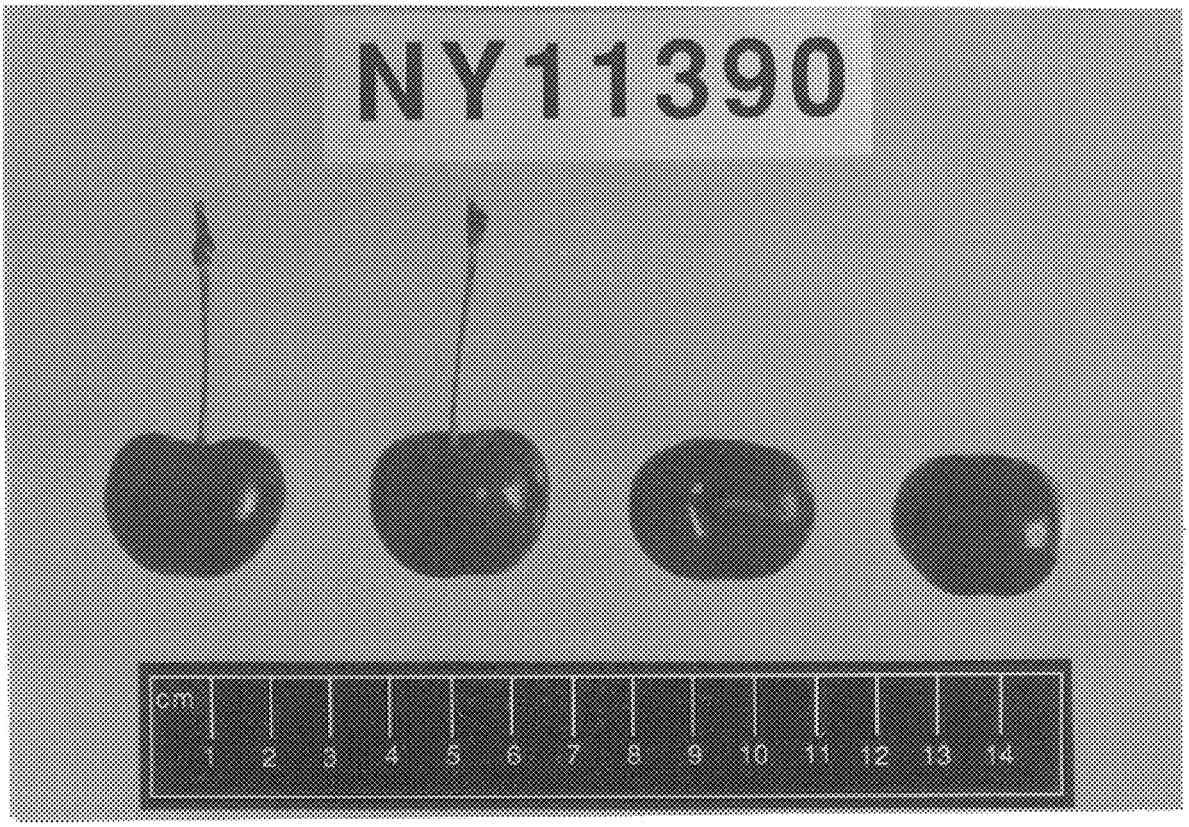
FIG. 2 shows fruit and pedicels of 'Royalton'.
Figure 3:
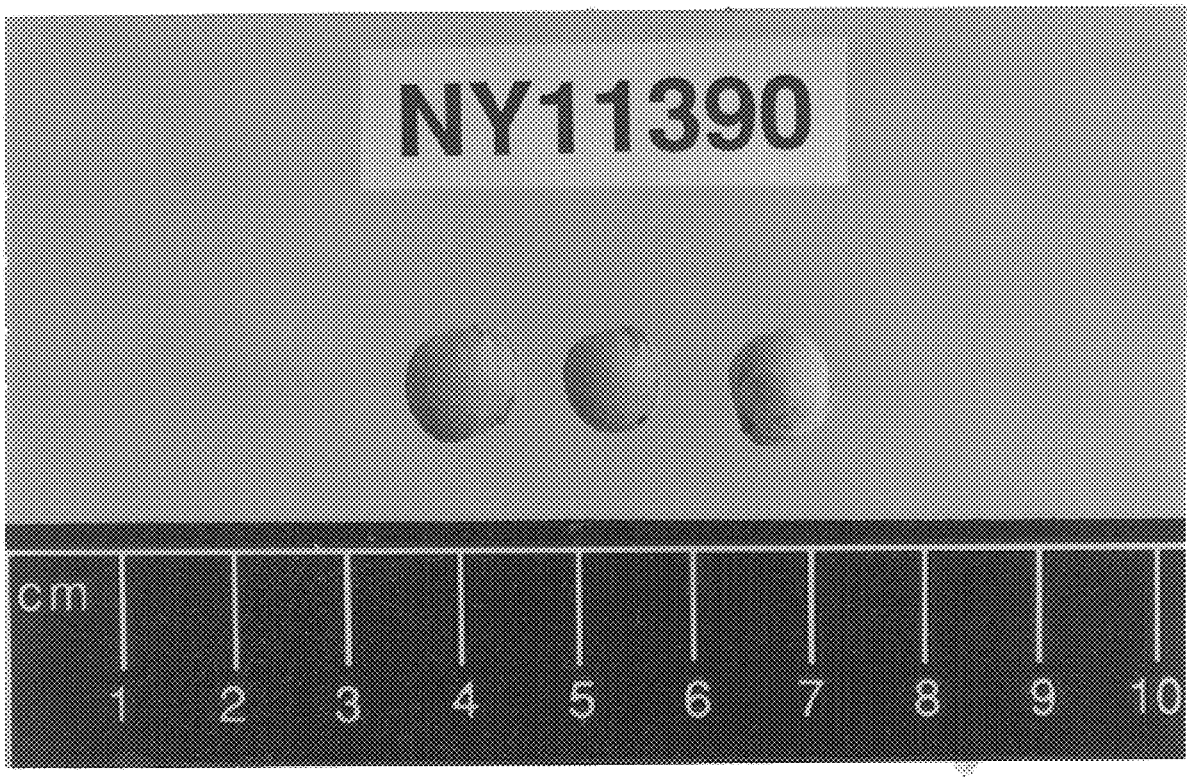
FIG. 3 shows pits of 'Royalton'.
Figure 4:
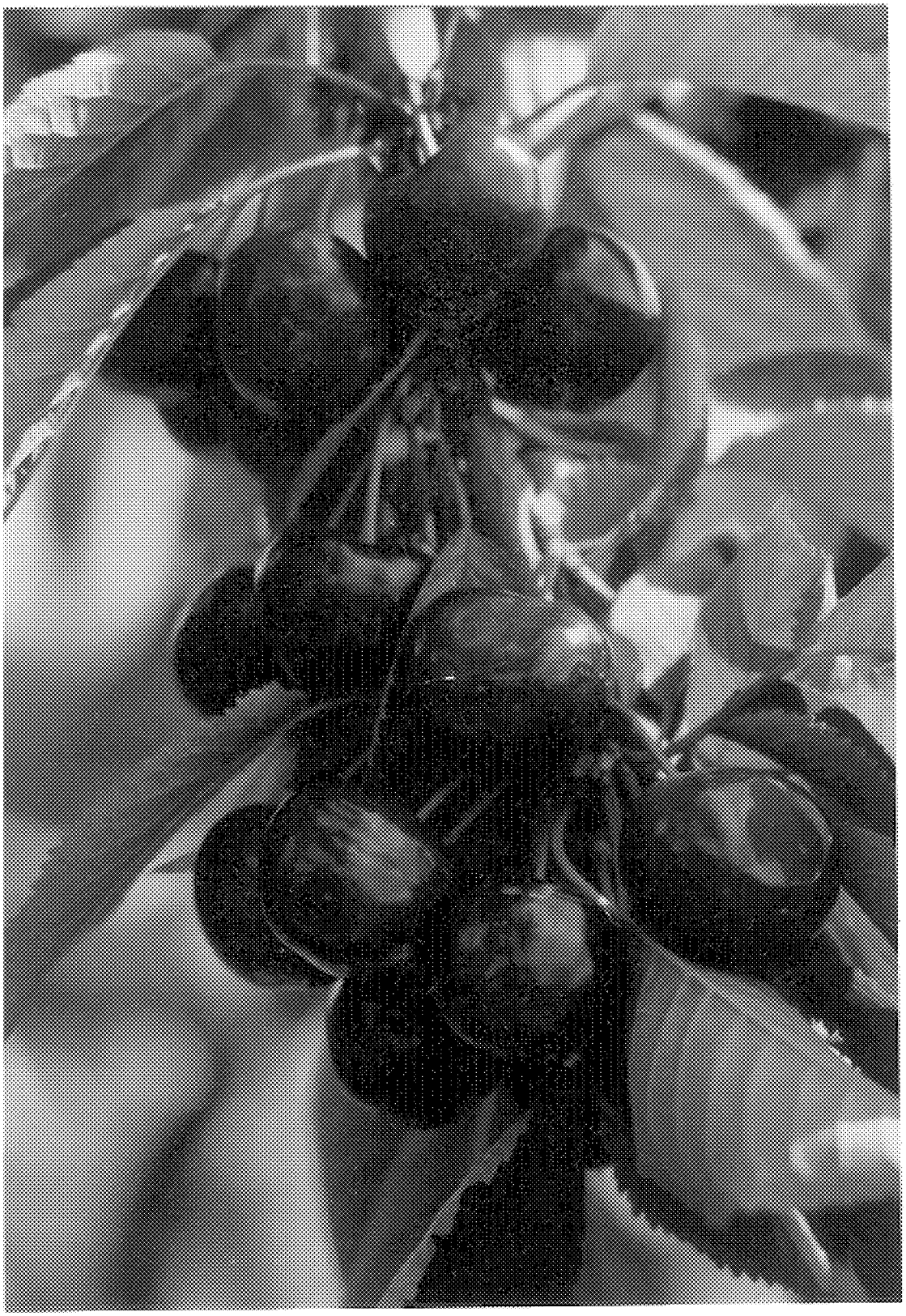
FIG. 4 shows fruit clustering of 'Royalton'.

The individual fruits of 'Royalton' (FIG. 2) are round-oblate, their skin color at maturity is greyed-purple 187A. Their flesh color is a slightly lighter shade of greyed-purple 187B. As indicated in FIG. 2, the suture of 'Royalton' is very slightly indented or else it is nearly as flat as the opposite non-suture side of the fruit. Fruits are uniform in the slightly oblate horizontal dimension of their two cheeks and quite flat sided on the suture and opposite, non-suture aspects of their horizontal dimension. Fruits have a very uniform large size compared to most other sweet cherry cultivars, usually averaging over 10 grams per fruit. They are about 3 cm diameter wide ×2.8 cm long (stem end to pistillate end). The stem cavity of 'Royalton' is shallow and wider than that of 'Hartland' and more closely resembles the 'Bing' cultivar in this aspect of its shape. Pits (FIG. 3) are large, round to round-conic. Pit color is greyed-orange 165D and surface characteristics are oblate shape the same as for 'Bing'. FIG. 4 shows a typical cluster of 'Royalton' fruit. Fruits resist moisture stress induced cracking in most seasons. The soluble solids level of 'Royalton' fruit usually exceeds 19% when they are grown in Geneva, NY. They have a rich, strong cherry flavor. They are firm, about 0.69 Instron units at maturity. They are somewhat crisp in texture (mouthfeel) at optimum maturity. They have a fruit removal force of about 554 grams of pull force. Thus 'Royalton' requires applications of plant growth regulators to "loosen" the fruits if this cultivar is processed with stems off. Since stems-on, processed fruit are highly important to the brining/maraschino industries that use "cocktail cherries", 'Royalton', with its high fruit removal force, would be ideal for this use with respect to stem retention, but yield potential is a disadvantage. Ripening days are about 58 after full bloom. Ripening for 'Royalton' is very uniform. Harvest dates for 'Royalton' for the years 1996, 1997 and 1998 averaged out to be July 4, compared to June 30 for 'Hartland' and July 14 for 'Somerset'.

Tree Habit

'Royalton' tree habit is vigorous, upright with few lateral branches produced along the proximal portions of ninety percent of the previous season's growth. This tree habit and branching structure leads to a "leggy" tall pyramid form. The tallest trees seen are on Mazzard rootstocks and to date are 20 feet tall and still growing upwardly. On 'Gisela 5' rootstock and 'Inmil' rootstock, both of which are amongst the most dwarfing of commercially available rootstocks for sweet cherries, the trees have topped out at about 14 feet.

Shoots

'Royalton' shoots are long with few lateral branches. They have many large lenticels. In the autumn, after cessation of terminal growth extension, the color of the bark at the fourth intenode above the proximal position is Greyed-orange 165A on the side of the stem which is commonly exposed to direct sunlight. The color of the other side of the stems at the same position is Greyed-brown 199A. These colors contrast to Greyed-orange 165B and Greyed-brown 199B for the Bing cultivar. Current season shoot growth often has characteristic grooves in the wood (bark and xylem) extending back from the terminal bud toward the proximal end for the first 9 to 10 distal bud positions.

Leaves

Figure 5:
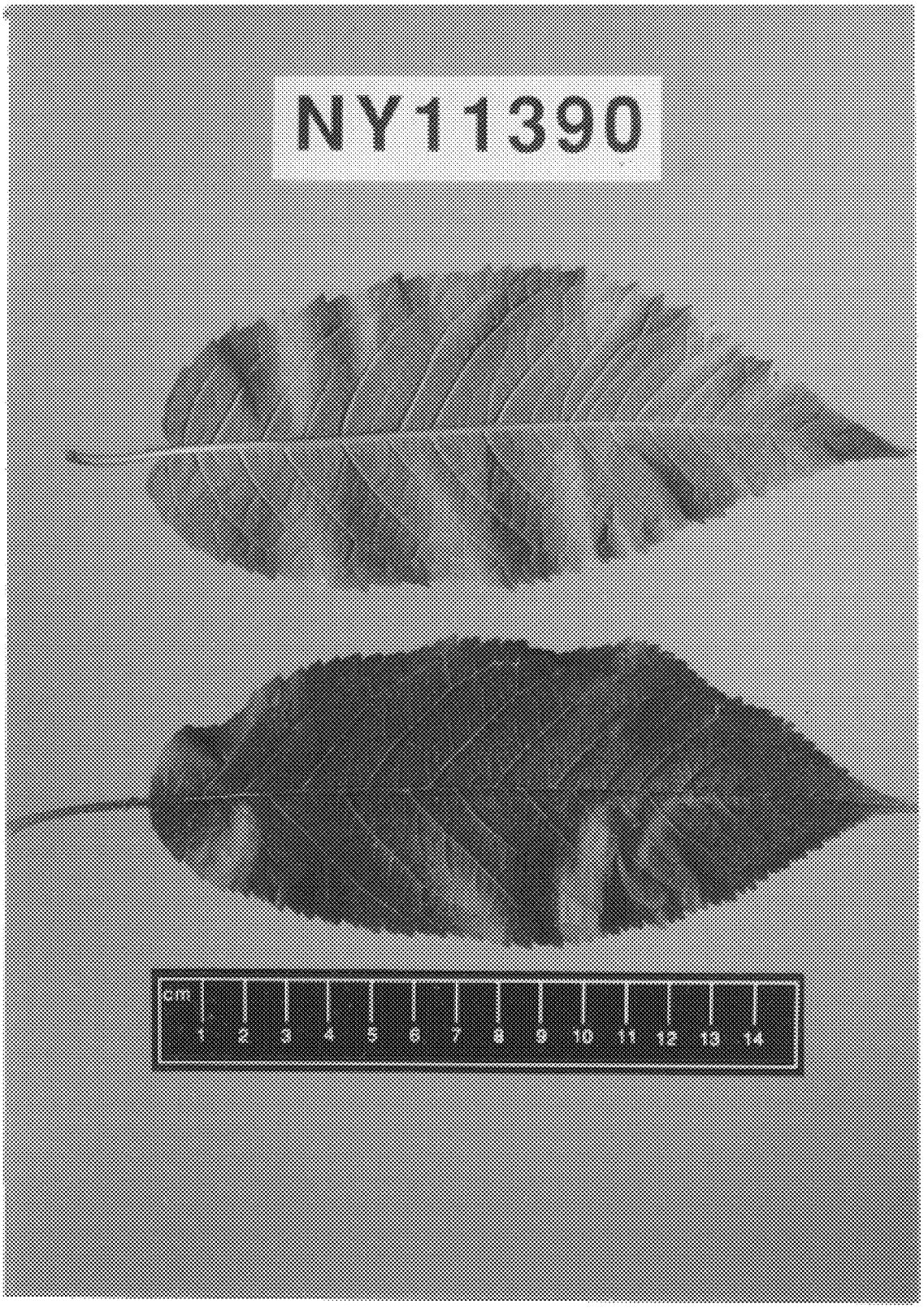
FIG. 5 shows the front and back view of two 'Royalton' leaves.

Leaves of 'Royalton' are large (FIG. 5); usually symmetrical; lamella glabrous and smooth with adaxial lamella surface dark green 137A; abaxial surface yellow-green 148B; and margin coarsely serrate, 3 to 4 serrations per cm; glands reniform, base usually 2 cm wide; stipules present during early stages of growth but abscissing before fruit harvest season. Petiole 4 to 4.5 cm; leaf poise typically 60 to 80 degrees from shoot.

Usefulness

'Royalton' sweet cherry is well suited for production to fulfill fresh market demands in most commercial cherry sites where we have tested its performance. Its large fruit size, high quality, dark, glossy external appearance and the good tolerance to water stress induced fruit cracking make it uniquely well suited to some areas of commercial production. 'Royalton' fruit are firmer and less prone to bruising during harvest and handling than the 'Summit' cultivar, which is the primary competitor for 'Royalton' in the eastern fruit growing districts. It is similar in fruit handling characteristics to the 'Ulster' and 'Kristin' cultivars, but since 'Royalton' has larger fruit,it is preferred over 'Ulster' and 'Kristin' for fresh market uses. 'Royalton' as well as 'Summit', 'Ulster' and 'Kristin' are more prone to fruit bruising than the fruit of 'Bing', which is the standard western USA cultivar. "Freshness" of the stem color to remain bright green during shipping and marketing, is perceived by produce buyers to be a key trait for fresh cherry cultivars to succeed with the chain stores. 'Royalton' has a very "fresh" stem and is comparable to the 'Bing' cultivar in stem longevity traits. The tree of 'Royalton' is not a consistent producer of regular ample cropping when evaluated for this trait across many New York orchard sites in any given set of five years and compared to 'Hartland' and 'Somerset' cultivars. The tree of 'Royalton' sets moderate crops even in good cropping years and needs no crop load adjustment to size the fruit adequately. In our field observations of resistance to bacterial canker (caused by certain species of *Pseudomonas*) we have noted better resistance in 'Royalton' than many cultivars we have tested. 'Royalton' is particularly sensitive to a disorder termed 'blast' which is resisted by other cultivars of sweet cherries. "Blast" is caused by certain strains of Pseudomonas that are quite prevalent in New York State and is a condition that refers to the collapse of fruiting spurs soon after flower emergence due to systemic infections of the flower bud parts and cambial regions of the fruiting spurs. In spite of its irregular cropping pattern and sensitivity to "blast," those orchardists that have placed the highest value on the fruit quality and fruit size and good handling traits of 'Royalton' and who have orchards that are less prone to heavy annual infections of their 'Royalton' trees by "blast"-causing bacteria, continue to plant this cultivar.

We claim:

1. A new and distinct sweet cherry cultivar as herein described and illustrated.

* * * * *